US008468873B2

(12) United States Patent
Huber et al.

(10) Patent No.: US 8,468,873 B2
(45) Date of Patent: Jun. 25, 2013

(54) METHOD FOR CHARACTERISING THE KNOCK-RESISTANCE OF FUELS

(75) Inventors: Karl Huber, Eichstatt (DE); Johann Hauber, Neuburg (DE)

(73) Assignee: ROFA Laboratory & Process Analyzers, Kritzendorf (AT)

( * ) Notice: Subject to any disclaimer, the term of this patent is extended or adjusted under 35 U.S.C. 154(b) by 246 days.

(21) Appl. No.: 12/988,943

(22) PCT Filed: Apr. 22, 2009

(86) PCT No.: PCT/EP2009/054844
§ 371 (c)(1),
(2), (4) Date: Oct. 21, 2010

(87) PCT Pub. No.: WO2009/130254
PCT Pub. Date: Oct. 29, 2009

(65) Prior Publication Data
US 2011/0036147 A1    Feb. 17, 2011

(30) Foreign Application Priority Data
Apr. 22, 2008    (DE) ................. 10 2008 001 306

(51) Int. Cl.
*G01N 33/22*     (2006.01)

(52) U.S. Cl.
USPC ........................................................ 73/35.12

(58) Field of Classification Search
USPC ........................................................ 73/35.12
See application file for complete search history.

(56) References Cited

U.S. PATENT DOCUMENTS

| 2,888,822 | A | | 6/1959 | Burhans |
| 3,183,708 | A | | 5/1965 | Roddick |
| 4,163,385 | A | | 8/1979 | Kato et al. |
| 4,331,024 | A | | 5/1982 | Childs et al. |
| 4,402,212 | A | * | 9/1983 | Childs ........................ 73/35.02 |
| 5,386,722 | A | | 2/1995 | Meyer et al. |
| 5,633,798 | A | | 5/1997 | Kopp |

FOREIGN PATENT DOCUMENTS

WO    WO 2008/024663 A2    2/2008

OTHER PUBLICATIONS

Article—Knock Measurement for Fuel Evaluation in Spark Ignition Engines, C. Hudson et al., Dept. of Engineering Science, Oxford University, Apr. 26, 2000.
Article—A Method for the Predetermination of the Knocking Behavior of Gas Engines with translation.
Din EN ISO 5163, Jan. 2006.
Knock Investigation by Flame and Radical Species Detection in Spark Ignition Engine for Different Fuels, ScienceDirect, 2007.
Knock Rating of Gaseous Fuels in a Single Cylinder Spark Ignition Engine, C. Rahmouni et al, Elsevier, 2004.
Comparison of Cylinder Pressure Based Knock Detection Methods, K. Burgdorf et al., Society of Automotive Engineers, Inc., 1987.
International Preliminary Report on Patentability, Nov. 23, 2010.
German Patent Office Search Report, Apr. 14, 2009.
International Search Report, Sep. 17, 2009.

\* cited by examiner

*Primary Examiner* — Freddie Kirkland, III
(74) *Attorney, Agent, or Firm* — Dority & Manning, P.A.

(57) ABSTRACT

A method for characterizing the knock-resistance of a fuel using a test engine is disclosed, wherein the time versus cylinder pressure curve of the test engine during combustion of the fuel in the test engine is determined. This pressure signal is, in turn, compared with the corresponding pressure signal of at least one standard fuel of known knock-resistance.

27 Claims, 5 Drawing Sheets

METHOD FOR CHARACTERISING THE KNOCK-RESISTANCE OF FUELS

FIELD OF INVENTION

The invention relates to a method for characterizing the knock resistance of fuels via the use of a test engine.

BACKGROUND

Standard DIN EN 228 stipulates the minimum requirements for the characteristic values and properties for non-leaded types of gasoline. Table 1 shows an excerpt of the essential characteristic values for fuel.

TABLE 1

| Characteristic value | Unit | Requirements according to DIN EN 228 | | |
| --- | --- | --- | --- | --- |
| | | SuperPlus | Super | Normal |
| Density at 15° C. | Kg/m³ | | 720-775 | |
| Knock resistance | | | | |
| R.O.N. | | min. 98 | min. 95 | min. 91 |
| M.O.N. | | min. 88 | min. 85 | min. 82.5 |
| Lead content | mg/L | | max. 5 | |
| Distillation range* | % (V/V) | | | |
| Evaporated quantity | | | | |
| (Class A) | | | | |
| at 70° C., E70 | | | 20-48 | |
| at 100° C., E100 | | | 46-71 | |
| at 150° C., E150 | | | min. 75 | |
| Evaporated quantity | | | | |
| (Class D/D1) | | | | |
| at 70° C., E70 | | | 22-50 | |
| at 100° C., E100 | | | 46-71 | |
| at 150° C., E150 | | | min. 75 | |
| Final boiling point (FBP) | ° C. | | max. 210 | |
| (Class A/D/D1) | | | | |
| Volatility indicator VLI** | | | | |
| (VLI = 10 × VP + 7/E70) | | | | |
| Class D1 | Index | | max. 1150 | |
| Distillation residue | % (V/V) | | max. 2 | |
| Vapor pressure (DVPE) | kPa | | | |
| Class A | | | 45.0-60.0 | |
| Class D/D1 | | | 60.0-90.0 | |
| Evaporation residue | mg/100 mL | | max. 5 | |
| Benzene content | % (V/V) | | max. 1 | |
| Sulphur content | mg/kg | | max. 150 | |
| Oxidation stability | min | | max. 360 | |
| Copper corrosion | Extent of corrosion | | max. 1 | |

*Class A: May 1-September 30 (summer)
Class D: November 16-March 15 (winter)
Class D1: March 16-April 30 & October 1-November 15 (transition)
**Vapor Lock Index Especially important in all of this is knock resistance which is described with two characteristic numbers: the motor octane number (M.O.N.) and the research octane number (R.O.N.). Briefly, knocking can occur during combustion in any gasoline engine and cause extensive engine damage, if intense enough. For this reason, engine developers are required to prevent the non-uniform combustion that occurs during knocking. In other words, they must integrate knock control systems into engine controls and to proactively prepare the engine for the fuel's knock resistance. High octane numbers permit higher performance with a simultaneously higher degree of efficiency of the engine and, therefore, lower consumption. For these reasons, higher prices can also be fetched with higher-octane fuels, even though they have almost the same energy content (fuel value) as lower-octane fuels.

The worldwide determination of octane numbers is nowadays carried out empirically and according to standardized processes in the fuel producers' laboratories. Special one-cylinder test engines with a variable compression ratio that can be adjusted to the respective fuel quality are used for this purpose. The objective is to compare the knock intensity of the fuel being tested with fuels of a known octane number in order to determine its octane number. Interpolation between octane numbers may be necessary. The standard arbitrarily assigned octane number for isooctane is 100 and for n-heptane is 0. By mixing these components, a fuel can be produced that will have the same knock intensity as the fuel being tested. The octane number that is being determined for will then correspond to the volumetric share of isooctane in the fuel mixture. Only testing conditions differentiate between M.O.N. and R.O.N. All other process steps are the same and the same measuring techniques and test engine were used.

The degree of knock intensity is measured with an electric sensor (electronic detonation meter) attached to the engine's combustion chamber (FIG. 1) and an indicator (knock meter) displays the result. The knock intensity and frequency calculations are not performed with the measuring data, however. Research has shown that fuels with equal octane numbers can actually have a different knock behavior regarding intensity and frequency. If this method is professionally applied with the corresponding experience, an accuracy of no more than +0.2 octane numbers can be achieved. The operation is done manually and takes between 20 and 30 minutes per octane number. There have been—and still are—many attempts to determine the octane number with calculations or another instrument—i.e., outside the engine. Unfortunately, so far it has not been possible to achieve this with the desired accuracy. If the fuel composition is known, a gas chromatography analysis or infrared spectroscopy can give reasonably accurate results, but these methods are only used in refineries because they know exactly the composition of their fuel. A fundamental improvement of the device and method has not yet been found.

The following problems have been detected in assessing the valid processes for determining the octane number:

The accuracy of the process can be improved upon.

The process is time-consuming; it cannot be automated and allows no online indication.

In the process, the knock intensity is indicated directly after the analog processing of the measuring signal. No exact calculation of the knock intensity and frequency takes place.

Whether the determined octane numbers actually reflect the knocking resistance of the fuels that current combustion engines require has been called into question.

It is, therefore, an object of the invention to create a process that will provide a fast and reliable characterization of the knock resistance of fuels possible.

SUMMARY

Objects and advantages of the invention are set forth in part in the following description, or may be obvious from the description, or may be learned through practice of the invention.

The objective is solved by determining the chronological sequence of the testing engine's cylinder pressures during the combustion of the fuel in the test engine so the determined pressure signals can be compared with the corresponding pressure signals of at least one standard fuel of known knock resistance.

The utilization of modern measuring and analytical techniques allows the exact characterization of the various parameters of the knocking combustion processes that occur in the test engine, such as knock intensity, knock pressure amplitude of the peak pressure, speed of pressure increase, and the frequency and the frequency distributions of these parameters. The approach taken and the necessary measuring techniques are described in the following exemplary embodiments.

DESCRIPTION

Figure 1:
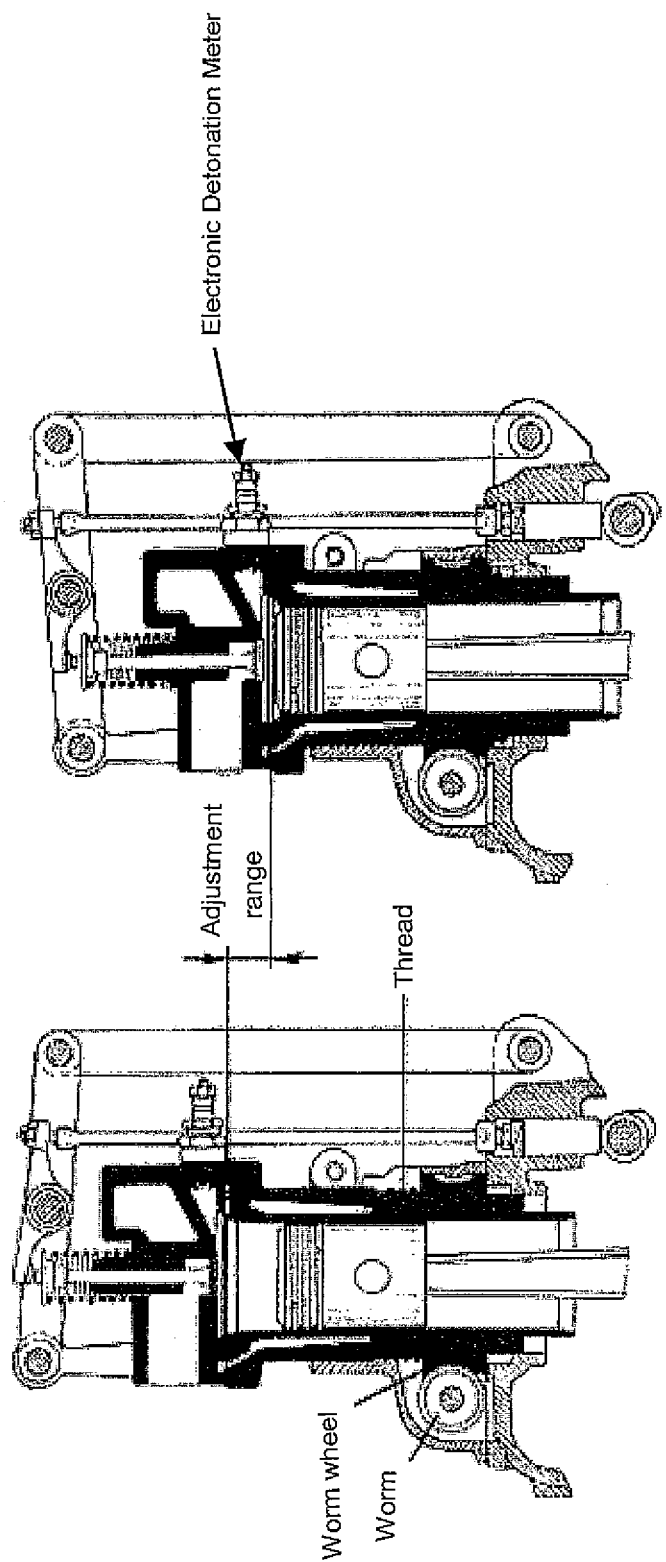
FIG. 1 shows a cross section of a test engine according to the invention.
Figure 2:
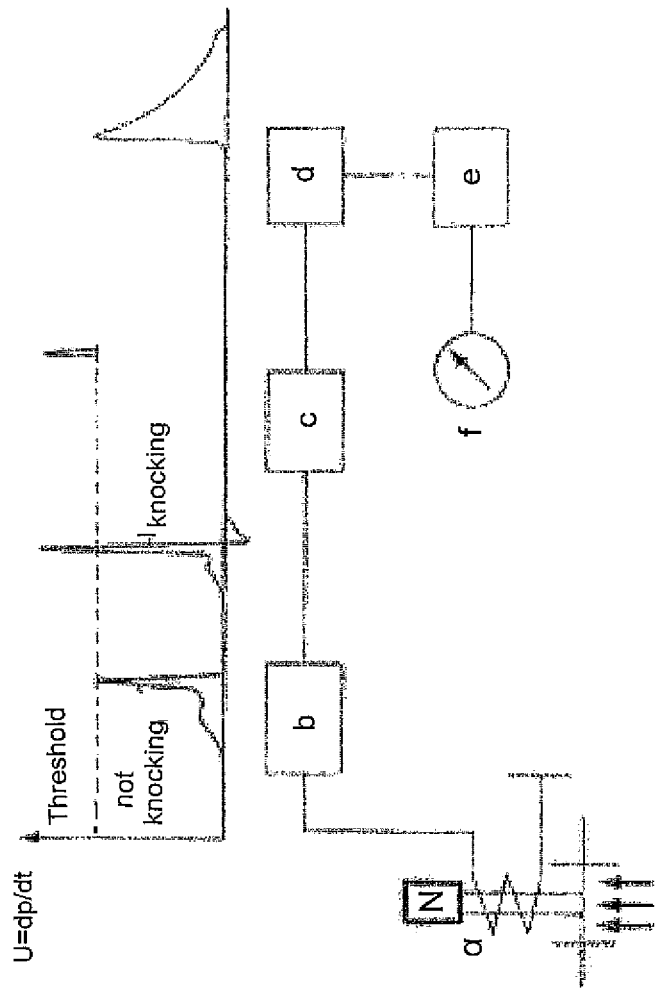
FIG. 2 shows a diagram of an electric knock sensing device according to the invention.

Reference is now made to particular embodiments of the invention, one or more examples of which are illustrated in the drawings. Each embodiment is provided by way of explanation of the invention, and not as a limitation of the invention. For example, features illustrated as described as part of one embodiment may be used with another embodiment to yield still a further embodiment. It is intended that the present invention include these and other modifications and variations.

Figure 3:
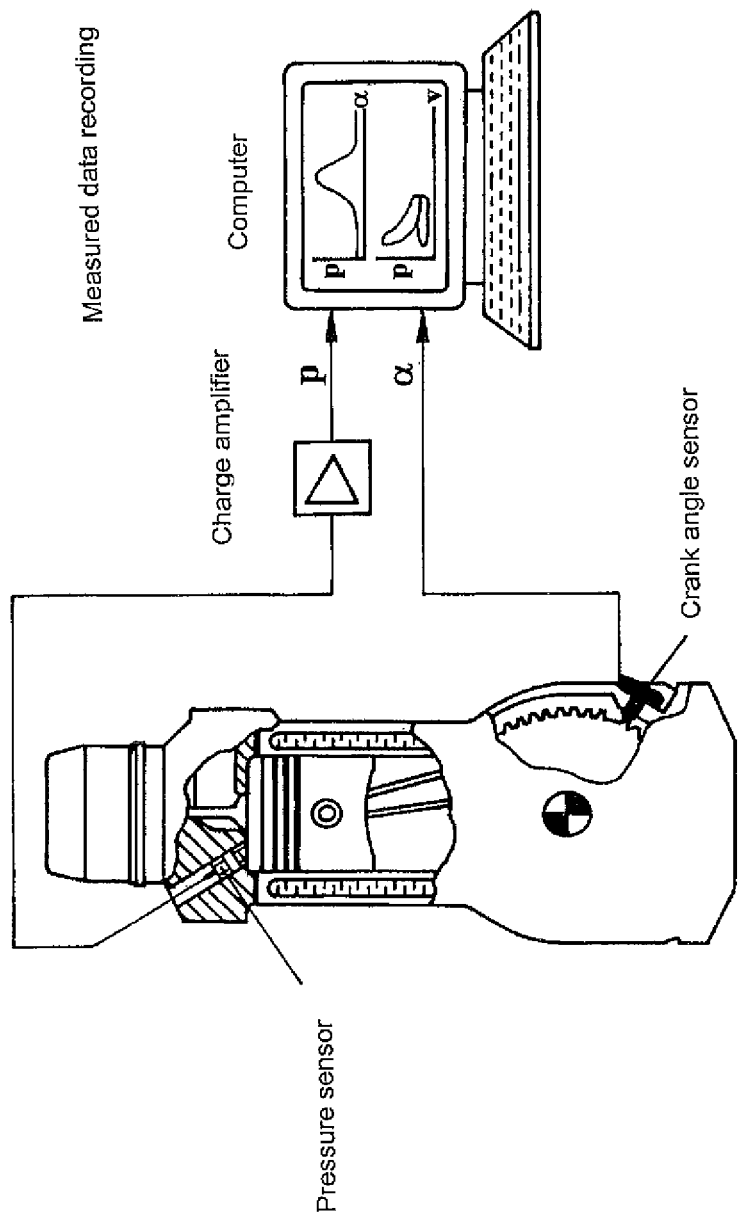
FIG. 3 shows an alternative embodiment of the knock sensing device according to the invention.

In one embodiment, a piezoelectric pressure sensor (as typically used by engine developers in their R&D tasks) is advantageously coupled with the combustion chamber, instead of the electronic detonation meter. Thus, the pressure signal is amplified and converted to a charge signal proportional to the cylinder pressure (p) (see FIG. 3). The charge signal is fed to a fast data capture unit, where it is digitalized, processed further, and then saved.

In this context, it can be advantageous if the pressure signals are filtered via a band pass filter (especially within the 3 to 15 kHz range and/or with high pass from 3 kHz) before comparing them to the corresponding signals of one or several standard fuels.

Figure 4:
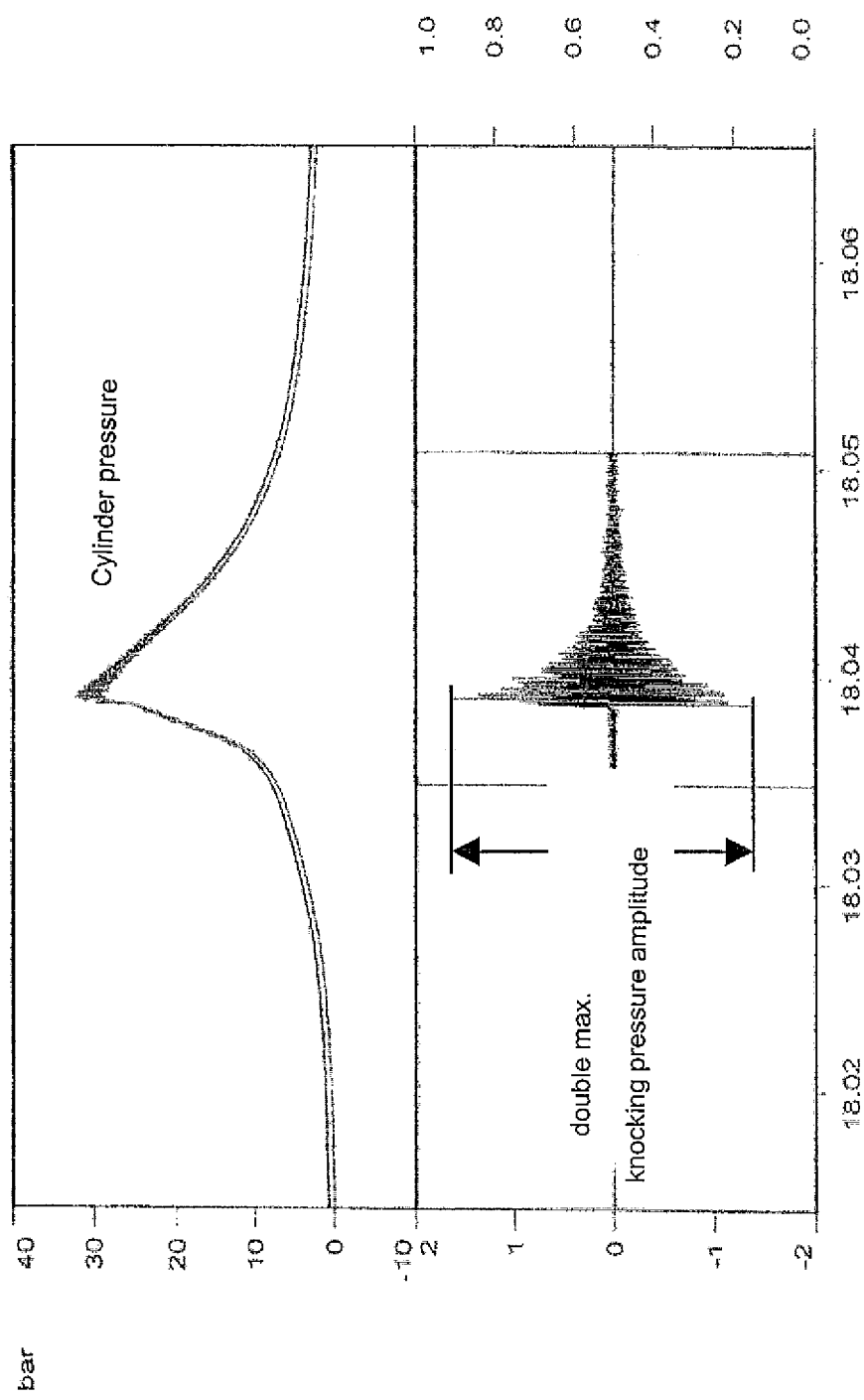
FIG. 4 shows an exemplary graph of crankshaft angle versus cylinder pressure according to the invention.

At the same time, it is also advantageous if the chronological sequence of the crankshaft angles ($\alpha$ in FIG. 3) of the test engine is determined during combustion via a crankshaft angle sensor. Using this information, the determined pressure signals can be analyzed either as a function of time, crankshaft angle, or ignition timing. FIG. 4 shows a representation of the cylinder pressure and the respective, time-dependent knock pressure amplitudes as a function of crankshaft angle.

Figure 5:
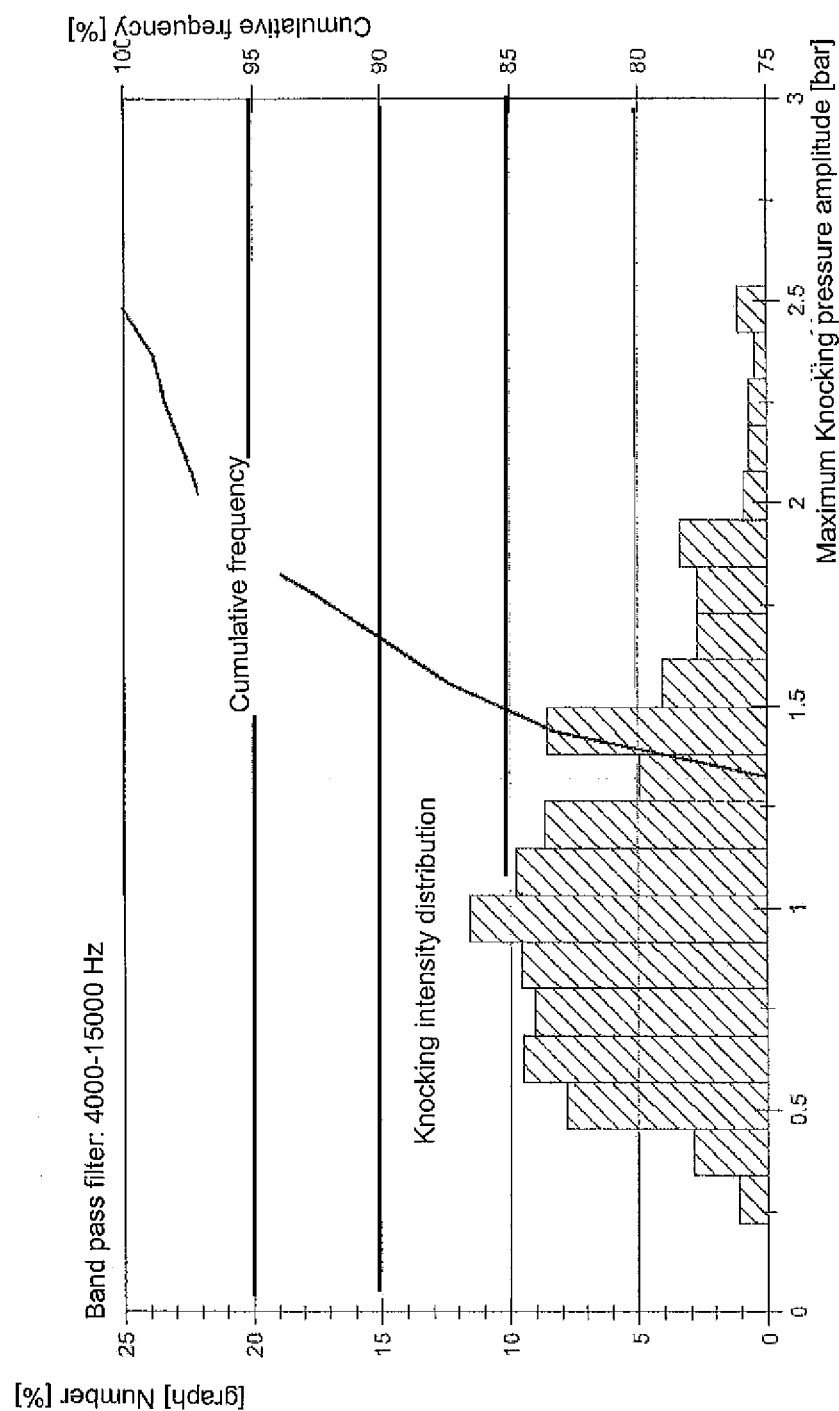
FIG. 5 shows an exemplary graph of knock intensity distribution according to the Invention.

Knock intensity or the other parameters mentioned above that can be derived from the cylinder pressure sequence and their distribution as a histogram, cumulative frequency or individual characteristic number can be displayed for describing the knocking (FIG. 5). Even a comparison of the individual parameters is possible, as important knowledge about the knock behavior of the examined fuel can be gained. In this respect, it must be pointed out that the respective operating conditions of the tested engine must be considered when interpreting the captured data to prevent false results.

A comparison of the corresponding results with those from typical standard fuels such as isooctane and/or n-heptane obtained in an analogous way leads to one or several characteristic numbers that describe the exact knocking resistance of the fuel to be tested.

In this case, the respective characteristic numbers based on the chronological sequence of the test engine's cylinder pressure signal that are obtained can be measured either during the individual test engine cycle or obtained from the statistical evaluation of the pressure signals of several cycles.

In addition, it is also advantageous if the compression ratio of the test engine is calculated based on the cylinder pressure at a defined crankshaft angle, whereby the crankshaft angle serves as a measure of the ignition timing. Since the knock behavior of a fuel depends, among other things, from the test engine's compression ratio, it is advantageous to take this parameter into account when comparing the pressure signals of the fuel tested with those of the standard fuel of known knock resistance.

Furthermore, it is also extremely advantageous if the measured cylinder pressure signals and the corresponding additional known data from the tested fuel—such as, for example, its exact chemical composition—can be stored in a database. After all, these measured values are the basis for future evaluations of new or not yet analyzed fuels. In this case (and especially while complying with standardized process steps), fast and reliable conclusions about the knock behavior of a fuel to be tested can be obtained. With the corresponding data stock, an analysis of standard fuels is therefore no longer necessary in every case.

Examples of the process steps are listed below:

Time-based measurement of the cylinder pressure signal (scanning frequency: 100 kHz).

Band pass filtration of the measured pressure signal (3 to 15 kHz).

Determination of the maximum amplitude height of the filtered pressure signal per cycle (best results with a signal processor).

Evaluation of the amplitude height and its frequency in an adjustable time window (300 cycles, intensity distribution, or cumulative frequency).

Correlation of results with the known standard fuels or their mixtures.

Display and storage of the correlation indices as a measure for knock resistance.

The important advantages of the device and the process include:

Higher accuracy, especially through the use of precision technology and statistical analysis.

More exact evaluation of the knock processes through the analysis of knock intensity and frequency.

Possibility of automation.

Online display of the characteristic number of the knock resistance.

Automatic or partially-automatic process.

Measurement with standard fuels no longer needed as soon as the results have been made available in a database.

The compression ratio can be exactly calculated from the pressure sequence occurring before the time of ignition.

Modifications of the invention are easily possible within the framework of the patent claims, in which case, it is expressly mentioned that all individual characteristics in the patent claims, in the description, and in the figures can be used in any combination thereof, as long as it is possible and makes sense. For example, it can be quite advantageous if the pressure and/or temperature of the combustion mixture and its dwelling time (especially in form of a characteristic number calculated therefrom) can be taken into account. It is advantageous if the ignition timing and the start of knocking of the combustion mixture can be recorded (especially via a sensor) and the intermediate time difference and/or the difference of the respective crankshaft angles of the test engine are considered. In this way, it is possible to very accurately determine the time period to be analyzed, which results in an especially reliable implementation of the test. In addition, it is also possible to determine the combustion period (heat input through combustion) of an individual or several test engine cycles for obtaining, therefrom, the ignition delay, the preliminary ignition, the maximum combustion speed and/or the residual amount of the combustion mixture from fuel and combustion gas, especially combustion air, when the knocking starts. The combustion period of an individual or several cycles of the test engine can also be determined (and at least a pre-defined value of the combustion period such as the start of combustion) via at least one sensor, especially one for measuring the ionic current inside the test engine, a sensor for measuring the structure-borne noise of the test engine, and/or an optical sensor. This method allows the very precise determination of the start of the combustion so that the period for the corresponding cylinder pressure measurement can be determined with exemplary reliability. It is, likewise, extremely advantageous for the characterization of knock resistance to include a statistical analysis of the measured parameters (especially those of the pressure signals), in which case this statistical analysis should encompass the recording of the measured parameters (especially of the pressure signals) of one or several cycles (between 200 and 500, for example), of the test engine, particularly in a defined operating point of the test engine. It would also be advantageous for the statistical analysis to encompass the calculation of the mean values of the measured parameters, so that possible measurement fluctuations should only have a minimal effect on the characterization of knock resistance.

Modifications and variations can be made to the embodiments illustrated or described herein without departing from the scope and spirit of the invention as set forth in the appended claims.

The invention claimed is:

1. A method for characterizing knock resistance of a fuel, comprising:
   burning a fuel to be tested in a test engine and determining a chronological sequence of a test engine cylinder pressure as the test fuel is burned; and
   comparing the determined pressure signals with corresponding pressure signals of at least one standard fuel of known knock resistance based on a frequency distribution of one or more characteristic parameters of the determined pressure signals.

2. The method according to claim 1, wherein isooctane and/or n-heptane is used as standard fuel.

3. The method according to claim 1, wherein at least one characteristic number is determined by comparing the pressure signals of the tested fuel and the fuel of known knock resistance, and wherein this number serves as a measure for the knock resistance of said tested fuel.

4. The method according to claim 1, wherein any combination of pressure, temperature, or dwell time of the combustion mixture of fuel and combustion gas of the test engine are taken into account in determining the knock resistance of the tested fuel.

5. The method according to claim 1, wherein the pressure signals of the tested fuel and the fuel of known knock resistance are filtered before the comparison via band pass filtering within the range of 3 to 15 kHz or with high pass filtering from 3 kHz.

6. The method according to claim 1, wherein ignition timing and the start of knocking of the combustion mixture of tested fuel and combustion gases are recorded via a sensor, and an intermediate time difference or a difference of the respective test engine crankshaft angles are computed.

7. The method according to claim 1, wherein the pressure signals of the tested fuel and fuel of known knock resistance are compared to one another based on their knock pressure amplitudes.

8. The method according to claim 1, wherein the pressure signals of the tested fuel and fuel of known knock resistance are compared to one another based on their peak pressures.

9. The method according to claim 1, wherein the pressure signals of the tested fuel and fuel of known knock resistance are compared to one another based on their pressure increase speeds.

10. The method according to claim 1, wherein the pressure signals of the tested fuel and fuel of known knock resistance are compared to one another based on their frequencies.

11. The method according to claim 1, wherein the pressure signals of the tested fuel and fuel of known knock resistance are compared to one another based on their knock intensities.

12. The method according to claim 1, wherein the pressure signals of the test engine cycles for the tested fuel and fuel of known knock resistance are compared with one another.

13. The method according to claim 1, wherein a combustion period of an individual or several measured cycles of the test engine is determined and used for obtaining any combination of an ignition delay, a preliminary ignition, a maximum combustion speed, or a residual amount of the combustion mixture made up of fuel and combustion gas when the knocking starts, which are taken into account during the characterization of the knock resistance.

14. The method according to claim 1, wherein the combustion period of an individual or several measured cycles of the test engine is determined and at least one of an ignition delay, a preliminary ignition, a maximum combustion speed, or a residual amount of the combustion mixture made up of fuel and combustion gas is determined with any one or combination of a sensor for measuring ionic current inside of the test engine, a sensor for measuring structure-borne noise of the test engine, or an optical sensor, and are taken into account during the characterization of the knock resistance.

15. The method according to claim 1, wherein pressure signals of several test engine cycles are determined and compared with one another.

16. The method according to claim 1, wherein the characterization of the knock resistance includes a statistical analysis of measured pressure signals.

17. The method according to claim 16, wherein the statistical analysis encompasses recording of the measured pressure signals of one or several test engine cycles in a defined operating range of the test engine.

18. The method according to claim 16, wherein the statistical analysis encompasses the calculation of mean values of the measured pressure signals.

19. The method according to claim 16, wherein the statistical analysis encompasses the determination of a frequency distribution of the pressure signals, knock pressure amplitudes, peak pressures, pressure increase speeds, frequencies, or knocking intensities.

20. The method according to claim 1, wherein the cylinder pressure is determined via a piezoelectric pressure sensor.

21. The method according to claim 1, wherein a chronological sequence of the test engine crankshaft angles is determined during combustion via a crankshaft angle sensor.

22. The method according to claim 21, wherein the test engine compression ratio is calculated based on the cylinder pressure at a defined crankshaft angle.

23. The method according claim 1, wherein pressure signals of the tested fuel and fuel of known knock resistance are compared to one another, taking into account a mass of the fuel injected into the test engine or the combustion gas.

24. The method according to claim 1, wherein pressure signals of the tested fuel and fuel of known knock resistance are compared to one another, taking into account the intake temperature of the combustion gas or the mixture of combustion gas and fuel.

25. The method according to claim 1, wherein pressure signals of the tested fuel and fuel of known knock resistance are compared to one another, taking into account an intake pressure of the combustion gas or the mixture of combustion gas and fuel.

26. The method according to claim 1, wherein pressure signals of the tested fuel and fuel of known knock resistance are compared to one another, taking into account a number of revolutions completed by the test engine.

27. The method according to claim 1, wherein determined pressure signals of the tested fuel and fuel of known knock resistance are recorded in a database as a function of a crankshaft angle or a compression ratio.

* * * * *